United States Patent
Duchamp et al.

(10) Patent No.: US 7,273,487 B1
(45) Date of Patent: Sep. 25, 2007

(54) BALLOON CATHETER HAVING A MULTILAYERED SHAFT WITH VARIABLE FLEXIBILITY

(75) Inventors: Jacky G. Duchamp, Flagstaff, AZ (US); Keith G. Sanders, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 669 days.

(21) Appl. No.: 10/741,773

(22) Filed: Dec. 18, 2003

(51) Int. Cl.
*A61M 29/00* (2006.01)

(52) U.S. Cl. ............ 606/194; 604/96.01; 604/525

(58) Field of Classification Search ........... 606/194, 606/103; 604/96–96.01, 103.09, 525, 103
See application file for complete search history.

(56) References Cited

U.S. PATENT DOCUMENTS

| | | | |
|---|---|---|---|
| 4,282,876 A | 8/1981 | Flynn | |
| 4,385,635 A | 5/1983 | Ruiz | |
| 4,888,146 A | 12/1989 | Dandeneau | |
| 4,921,483 A * | 5/1990 | Wijay et al. | 604/103.1 |
| 4,976,690 A | 12/1990 | Solar et al. | |
| 5,047,045 A | 9/1991 | Arney et al. | |
| 5,085,649 A | 2/1992 | Flynn | |
| 5,308,342 A | 5/1994 | Sepetka et al. | |
| 5,370,655 A | 12/1994 | Burns | |
| 5,480,383 A | 1/1996 | Bagaoisan et al. | |
| 5,499,973 A * | 3/1996 | Saab | 604/96.01 |
| 5,614,136 A | 3/1997 | Pepin et al. | |
| 5,622,665 A | 4/1997 | Wang | |
| 5,725,814 A | 3/1998 | Harris | |
| 6,030,369 A * | 2/2000 | Engelson et al. | 604/264 |
| 6,045,547 A | 4/2000 | Ren et al. | |
| 6,193,686 B1 * | 2/2001 | Estrada et al. | 604/103.09 |
| 6,217,565 B1 | 4/2001 | Cohen | |
| 6,524,299 B1 * | 2/2003 | Tran et al. | 604/523 |
| 6,575,958 B1 * | 6/2003 | Happ et al. | 604/525 |
| 6,579,484 B1 | 6/2003 | Tiernan et al. | |
| 6,663,614 B1 | 12/2003 | Carter | |

* cited by examiner

*Primary Examiner*—Anhtuan T. Nguyen
*Assistant Examiner*—Pavitra Kotini
(74) *Attorney, Agent, or Firm*—Fulwider Patton LLP (57) ABSTRACT

A balloon catheter having a multilayered shaft with variable flexibility along the length of the shaft. In a presently preferred embodiment, the multilayered shaft has a multilayered outer tubular member and an inner tubular member, both the inner and outer tubular members having sections along which the flexibility and/or diameter of the tubular members decrease. These diameter and flexibility transition sections along the outer tubular member are preferably aligned with transitions along the inner tubular member, to provide improved catheter performance.

18 Claims, 4 Drawing Sheets

BALLOON CATHETER HAVING A MULTILAYERED SHAFT WITH VARIABLE FLEXIBILITY

BACKGROUND OF THE INVENTION

This invention generally relates to medical devices, and particularly to intracorporeal devices for therapeutic or diagnostic uses, such as balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g., greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

The progression of improvements in dilatation catheters generally has been to make catheters with lower profiles and with the proximal portions of the catheter shaft being much stiffer than the distal portions. However, this progression has also increased the difficulty in forming smooth transitions between the various sections of the catheter shaft, and a balance must be struck between the often competing considerations of force transmission (pushability), kink resistance, flexibility, and low profile.

What has been needed is a balloon catheter with a shaft having an improved combination of characteristics to provide improved catheter performance.

SUMMARY OF THE INVENTION

This invention is directed to a balloon catheter having a multilayered shaft with variable flexibility along the length of the shaft. In a presently preferred embodiment, the multilayered shaft has a multilayered outer tubular member and an inner tubular member, both the inner and outer tubular members having sections along which the flexibility and/or diameter of the tubular members decrease. These diameter and flexibility transition sections along the outer tubular member are preferably aligned with transitions along the inner tubular member, to provide improved catheter performance.

The balloon catheter generally includes an elongated shaft formed at least in part by the outer tubular member and inner tubular member, and a balloon sealingly secured to a distal section of the shaft. The shaft has an inflation lumen which is defined by the outer tubular member (e.g., the annular space between the inner surface of the outer tubular member and the outer surface of the inner tubular member therein) and which is in fluid communication with the balloon interior, and has a guidewire lumen defined by the inner tubular member.

The multilayered outer tubular member has at least first and second (e.g., inner and outer) layers, extending along at least part of the length of the outer tubular member. The first and second layers have different stiffnesses (e.g., are formed of polymers having different Shore durometer hardness values). In one presently preferred embodiment, the first and second layers extend the entire length of the outer tubular member, although in alternative embodiments, at least one of the first and second layers is shorter than the outer tubular member.

In a presently preferred embodiment, the multilayered outer tubular member has a relatively stiff proximal section with the first and second layers extending therealong in a first relative proportion which is preferably substantially constant, a relatively flexible distal section with the first and second layers extending therealong in a second relative proportion which is preferably substantially constant and which is different from the first relative proportion, and a transition section between the proximal and distal sections along which the relative proportion of the first and second layers inversely cotapers to transition from the first to the second relative proportion. The transition section has a proximal and a distal portion, and has a tapered portion along which the diameter of the outer tubular member decreases distally. Similarly, the distal section has a tapered portion along which the diameter of the outer tubular member again decreases distally.

The inverse cotaper in the transition section is preferably produced by extruding the first layer from an extruder having a first pump at an output end thereof, and extruding the second layer from a second extruder having a second pump at an output end thereof, which in a presently preferred embodiment is formed according to a method set forth in U.S. application Ser. No. 09/707,681 (Carter), incorporated by reference herein in its entirety. However, a variety of suitable conventional coextrusion systems can be used, such as those using on/off valves to control the flow of the polymers making up the two layers. Additionally, U.S. Pat. No. 5,725,814 (Harris), incorporated by reference herein in its entirety, discloses a coextrusion apparatus using gear pumps at the output ends of multiple extruders, which can be used to vary the relative amount of first and second layers. The gear pumps are used to vary the relative amount of the polymers extruded and to thus form an extruded tube having multiple layers, the proportions of which vary along the length of the extruded tube.

The shaft inner tubular member is preferably a multilayered tubular member formed of two or more polymeric layers. In a presently preferred embodiment, the inner tubular member has a proximal section, a distal section, and a tapered section extending between the proximal section and the distal section and along which the diameter of the inner tubular member decreases distally. In a presently preferred embodiment, the tapered multilayered inner member is formed according to a method set forth in U.S. Pat. No. 6,579,484 (Tiernan, et al.), incorporated by reference herein in its entirety, using a co-extrusion system including a puller with programmable tapering capabilities.

The multilayered outer tubular member transitions to distally decreasing flexibility and diameter, without the need for joining separate tubes together in an end-to-end fashion. Consequently, the stiffness and profile increases caused by such junctions are avoided in the catheter of the invention. The single piece multilayered outer tubular member is completely junctionless (i.e., no bonded junctions between individual longitudinal sections of the outer tubular member), as is the inner tubular member. With the absence of such junctions, the push applied at the proximal end of the shaft is steadily transmitted to the distal portion of the shaft.

The catheter has a shaft with a gradual increase in flexibility along the length of the shaft. Moreover, the catheter has optimized inflation/deflation and delivery properties, due at least in part to the multilayered transitioning tubular members and the alignment of one or more transitions of the outer member with a transition of the inner member. For example, in a presently preferred embodiment, the entire length of the inner tubular member tapered section is radially aligned with a location on the outer tubular member located in the transition section of the outer tubular member (i.e., at least part of the outer tubular member transition section extends coextensively with the entire length of the inner tubular member tapered section).

The catheter of the invention has excellent pushability, kink resistance, flexibility, and low profile, for improved ability to be advanced through a patient's tortuous anatomy and position the balloon or other distal end instrumentality across an occluded section of the blood vessel. These and other advantages of the invention will become more apparent from the following detailed description and accompanying drawings.

DETAILED DESCRIPTION OF THE PREFERRED EMBODIMENTS

Figure 1:
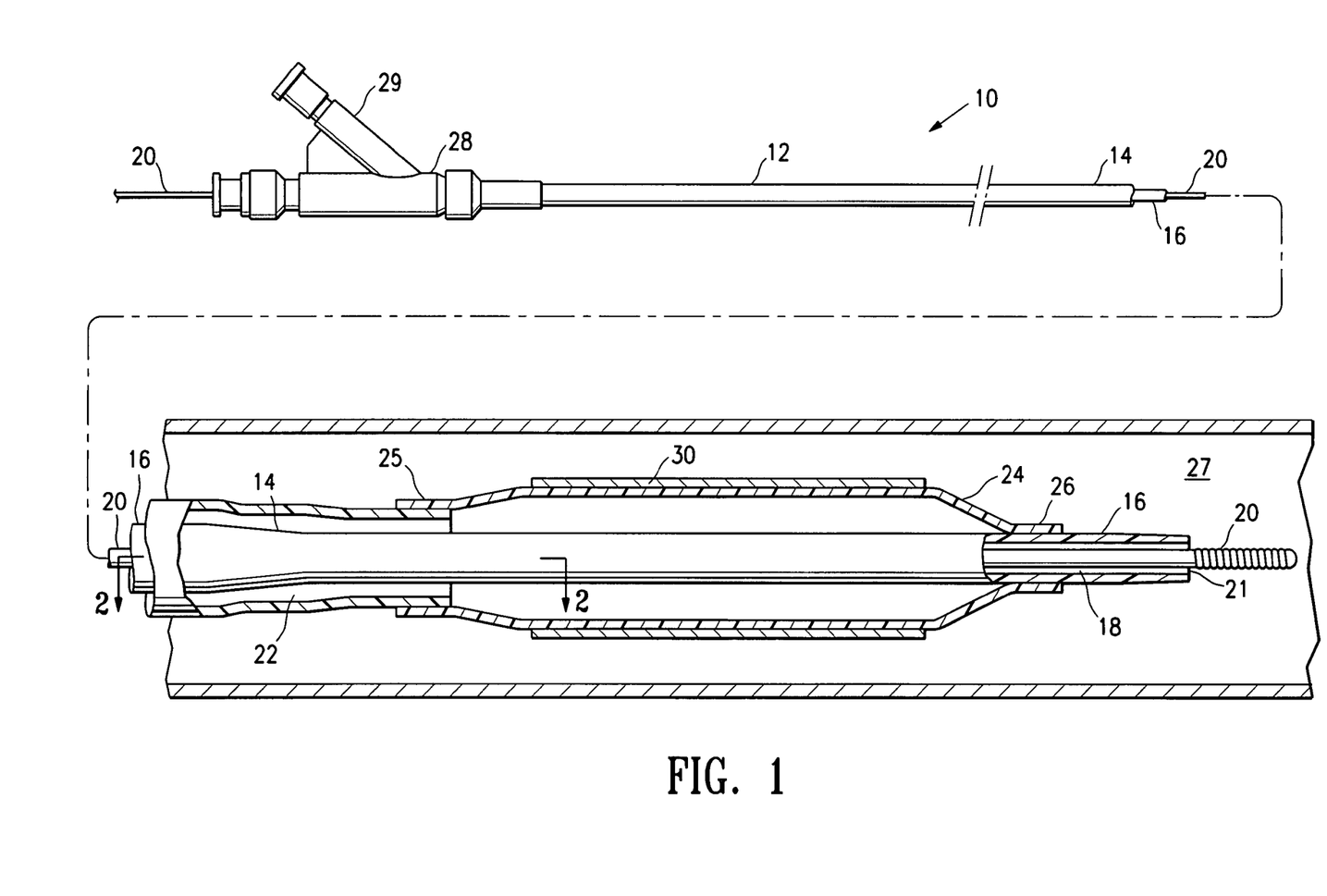
FIG. 1 is an elevational view, partially in section, of a stent delivery balloon catheter embodying features of the invention.
Figure 3:
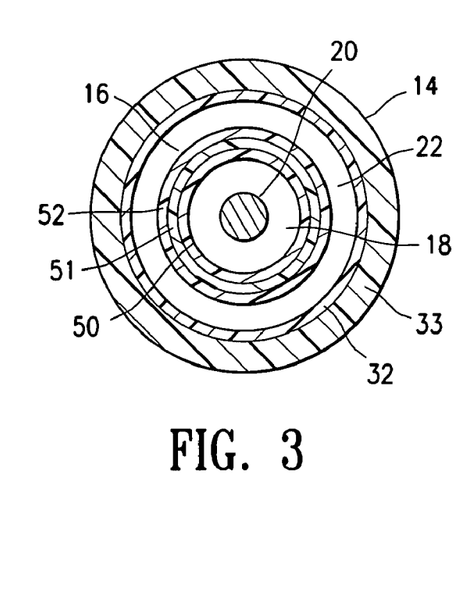
FIGS. 3-5 are transverse cross sectional views of the balloon catheter shown in FIG. 2, taken along lines 3-3, 4-4, and 5-5, respectively.
Figure 4:
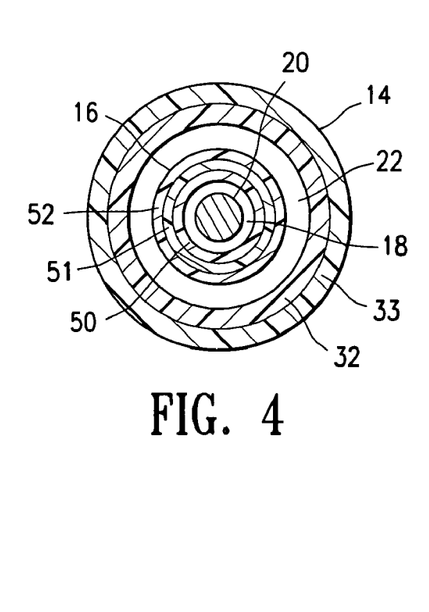
Figure 5:
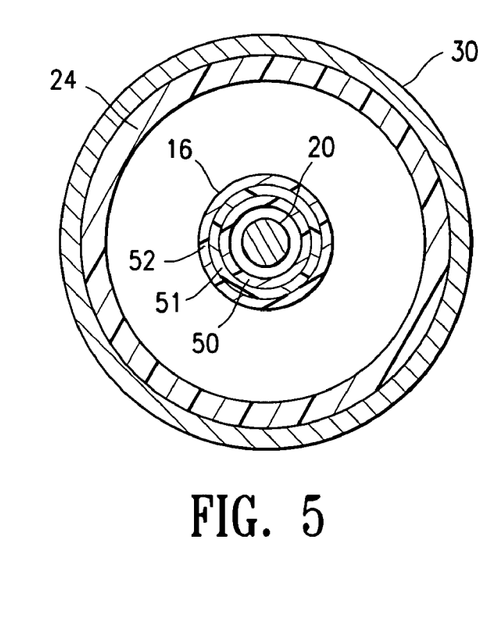

FIG. 1 illustrates an over-the-wire type stent delivery balloon catheter 10 embodying features of the invention. Catheter 10 generally comprises an elongated catheter shaft 12 having an outer tubular member 14, and an inner tubular member 16 extending in the outer tubular member 14 from the proximal to the distal end of the catheter shaft. Inner tubular member 16 defines a guidewire lumen 18 configured to slidingly receive a guidewire 20, and the outer tubular member 14 defines an inflation lumen 22, as best shown in FIG. 3 illustrating a transverse cross section of the distal end of the catheter shown in FIG. 1, taken along line 3-3. In the embodiment of FIG. 1, the inflation lumen 22 has an annular shape as a result of the coaxial relationship between outer tubular member 14 and inner tubular member 16. Guidewire 20 extends out the distal end of the catheter through a distal guidewire port 21. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 28 at the proximal end of catheter shaft 12 is configured to provide access to guidewire lumen 18, and to direct inflation fluid through arm 29 into inflation lumen 22. In the embodiment illustrated in FIG. 1, the balloon 24 is illustrated prior to complete inflation thereof, with an expandable stent 30 mounted on the working length of the balloon 24 for implanting within a patient's body lumen 27. The distal end of catheter 10 may be advanced to a desired region of the patient's body lumen 27 in a conventional manner, the balloon 24 inflated to expand stent 30, and the balloon deflated, leaving the stent 30 implanted in the body lumen 27.

Figure 2:
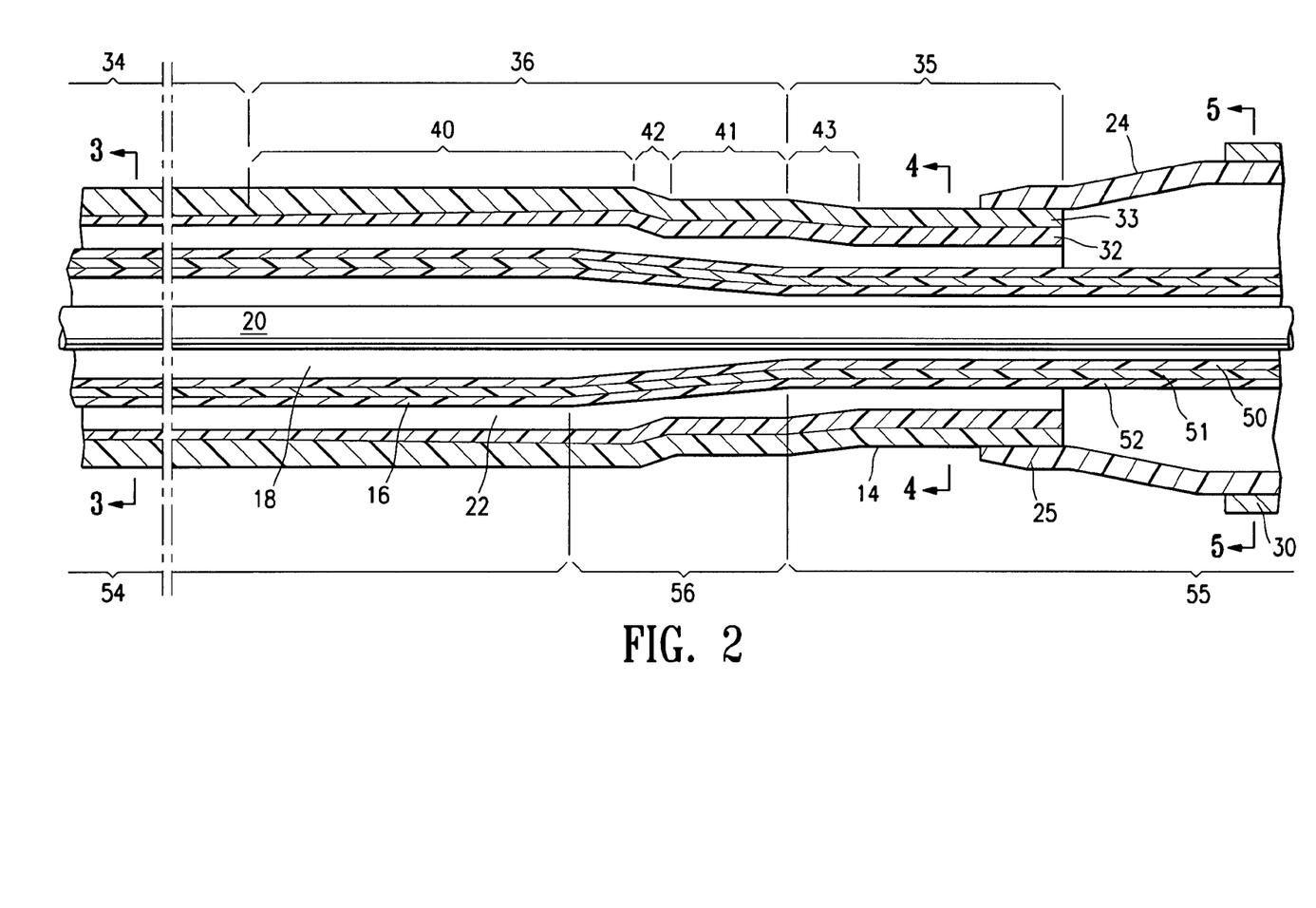
FIG. 2 is an enlarged, longitudinal cross sectional view of the balloon catheter shown in FIG. 1, taken along line 2-2.

FIG. 2 illustrates an enlarged, longitudinal cross sectional view of the balloon catheter shown in FIG. 1, taken along line 2-2. In the embodiment of FIG. 2, the outer tubular member 14 is multilayered with an inner layer 32 and an outer layer 33. The inner and outer layers 32, 33 are typically coextruded, and extend the entire length of the multilayered outer tubular member 14 in the embodiment of FIG. 2. The inner layer 32 is formed of a polymeric material having a different stiffness (e.g., a different Shore durometer hardness) than the outer layer 33. The thickness of each layer 32, 33 varies along the length of the outer tubular member 14, to thereby provide the multilayered outer tubular member with a distal section 35 which is more flexible than a proximal section 34. In the embodiment illustrated in FIG. 2, in order for the distal section 35 to be more flexible than the proximal section 34, the outer layer 33 is stiffer (e.g., is formed of a polymer having a high Shore durometer hardness) than the inner layer 32. Although discussed below primarily in terms of an embodiment in which the outer layer 33 is formed of a polymer having a higher Shore durometer hardness than the inner layer 32, it should be understood that in alternative embodiment (not shown), the inner layer 32 is stiffer than the outer layer 33, so that the relative proportions of the two layers as discussed in more detail below would be reversed.

The outer tubular member 14 has a transition section 36 which extends between and connects the distal end of the proximal section 34 and the proximal end of the distal section 35. The inner and outer layers 32, 33 inversely cotaper along the entire length of the transition section 36, to thereby transition from the relative proportion of the proximal section 34 to the relative proportion of the distal section 35.

In the illustrated embodiment, in the proximal section 34, the thickness of the outer layer 33 is about 75% of the total thickness of the two layers 32, 33, and the thickness of the inner layer 32 is about 25% of the total thickness of the two layers 32, 33 (i.e., the relative proportion of the inner and outer layers 32, 33 is about 25:75). In general, a suitable relative proportion of the inner and outer layers 32, 33 along the proximal section 34 in the embodiment of FIG. 2 is anywhere from about 5:95 to about 40:60, more specifically about 20:80 to about 30:70, depending on the nature of the polymers forming the layers 32, 33 and the desired catheter performance. In a presently preferred embodiment, the relative proportion of the inner and outer layers 32, 33 is constant along the entire length of the proximal section 34. However, in alternative embodiments (not shown), the relative proportion may transition to a different relative proportion within the proximal section 34. It should be understood that in an embodiment in which the outer layer 33 is formed of a more flexible polymer than the inner layer 32, the outer layer 33 would alternatively be about 25% of the total thickness of the two layers 32, 33 along the proximal section 34 in the embodiment of FIG. 2.

In the illustrated embodiment, the distal section 35 of the outer tubular member 14 has the inner and outer layers 32, 33 in a relative proportion of about 50:50. In general, a suitable relative proportion of the inner and outer layers 32, 33 along the distal section 35 is anywhere from about 40:60 to about 95:5, more specifically about 40:60 to about 60:40, depending on the nature of the polymers forming the layers 32, 33 and the desired catheter performance. Similar to the proximal section 34, in a presently preferred embodiment, the relative proportion of the inner and outer layers 32, 33 is constant along the entire length of the distal section 35, although it may alternatively vary.

The transition section 36 has a length greater than the distal section 35 and less than the proximal section 34 of the outer tubular member 14. In one embodiment, the transition section 36 is about 33 cm in length, the distal section 35 is about 15 cm in length, and the proximal section 34 is about 91 cm in length. The relatively long length of the transition section 36 provides a gradual change in the flexibility of the shaft as the proportion of the inner and outer layers 32, 33 changes there along.

In the illustrated embodiment, the transition section 36 of the outer tubular member 14 has a proximal portion 40, a distal portion 41, and a tapered portion 42 therebetween.

The inner diameter and outer diameter of the outer tubular member 14 decrease distally along the length of the tapered portion 42 of the transition section 36. Similarly, the inner and outer diameter of the outer tubular member again decrease distally along the length of a tapered portion 43 of the distal section 35. As a result, the inner diameter of the distal portion 41 of the transition section 36 is less than the inner diameter of the proximal portion 40 of the transition section 36 and is greater than the inner diameter of at least a portion of the distal section 35 of the outer tubular member 14, and the outer diameter of the distal portion 41 of the transition section 36 is less than the outer diameter of the proximal portion 40 of the transition section 36 and is greater than the outer diameter of at least a portion of the distal section 35 of the outer tubular member 14.

The tapered portions 42 and 43 are typically formed by necking the outer tubular member 14, by for example pulling the outer tubular member 14 down onto a tapered mandrel while heating at least part of the outer tubular member 14. The tapered portion 43 in the distal section 35 of the outer tubular member 14 provides a gradual decrease in the outer tubular member outer diameter. The entire length of the tapered portion 43 is typically about 1 to about 8 cm, more specifically about 4 to about 6 cm. Typically, the entire length of the tapered portion 43 is about 15% to about 50% of the entire length of the distal section 35. The tapered portion 42, located proximal to tapered portion 43, is typically less gradual, tapering distally over a length which in one embodiment is about 5 to about 30 mm, more specifically about 10 to about 20 mm. Typically, the entire length of the tapered portion 42 is about 5% to about 10% of the entire length of the transition section 36. In one embodiment, the wall thickness of the outer tubular member 14 is constant, or is substantially constant (i.e., changes by less than about 10% at tapered portions 42 and 43), along the length of the outer tubular member 14.

The inner tubular member 16 is preferably a multilayered tubular member. In the embodiment of FIG. 2, the inner tubular member has three layers, namely, an inner layer 50, middle layer, 51, and outer layer 52, of different polymeric materials extending from a proximal end to a distal end of the inner tubular member in a constant relative proportion. The multilayered inner tubular member 16 has a proximal section 54, a distal section 55, and a tapered section 56 extending between and connecting a distal end of the proximal section 54 and a proximal end of the distal section 55 and along which the inner diameter and outer diameter of the inner tubular member 14 decrease distally. Thus, the inner diameter of the distal section 55 of the inner tubular member 16 is less than the inner diameter of the proximal section 54 of the inner tubular member 16, and the outer diameter of the distal section 55 of the inner tubular member 16 is less than the outer diameter of the proximal section 54 of the inner tubular member 16.

At least part of the tapered section 56 of the inner tubular member 16, and preferably the entire length of the tapered section 56 of the inner tubular member 16 is radially aligned with a location on the outer tubular member located in the transition section 36 of the outer tubular member 14. In the illustrated embodiment, the distal end of the tapered section 56 is radially aligned with a location on the outer tubular member located at a proximal end of the tapered portion 43 of the distal section 35 of the outer tubular member 14. The proximal end of the tapered section 56 is radially aligned with a location on the outer tubular member 14 located in the proximal portion 40 of the transition section 36 of the outer tubular member 14.

In a presently preferred embodiment, the tapered section 56 of the inner tubular member 16 is formed during extrusion of the inner tubular member 16. The entire length of the tapered section 56 of the inner tubular member 16 is typically about 10% to about 25% of the entire length of the inner tubular member 16, and in one embodiment is about 18 to about 22 cm in length. In one embodiment, the wall thickness of the inner tubular member 16 is constant, or is substantially constant (i.e., changes (e.g., decreases) by less than about 10% at tapered section 56), along the length of the inner tubular member 16.

In a presently preferred embodiment, the outer layer 33 of the outer tubular member 14 is formed of a polyamide such as Nylon 12, and the inner layer 32 is formed of a polyamide block copolymer (PEBAX). The Nylon 12 has a higher Shore durometer hardness than the PEBAX. The Shore durometer hardness of the PEBAX is typically about 63D to about 72D, with the later being more preferred when the catheter 10 is a stent delivery catheter. The Shore durometer hardness of the Nylon 12 is typically about 70D to about 75D. In a presently preferred embodiment, the outer tubular member 14 consisting essentially of the inner and outer polymeric layers 32, 33 has sufficient force and torque transmission, so that a braided or coiled reinforcing layer is not provided in the wall of the outer tubular member 14. The inner tubular member inner layer 50 is typically a lubricious polymer such as HDPE or a fluoropolymer, the middle layer 51 is typically an adhesive polymer capable of bonding the inner and outer layers 50, 52 together, and the outer layer 52 is typically hot melt compatible with the polymeric material of the balloon 24.

Figure 6:
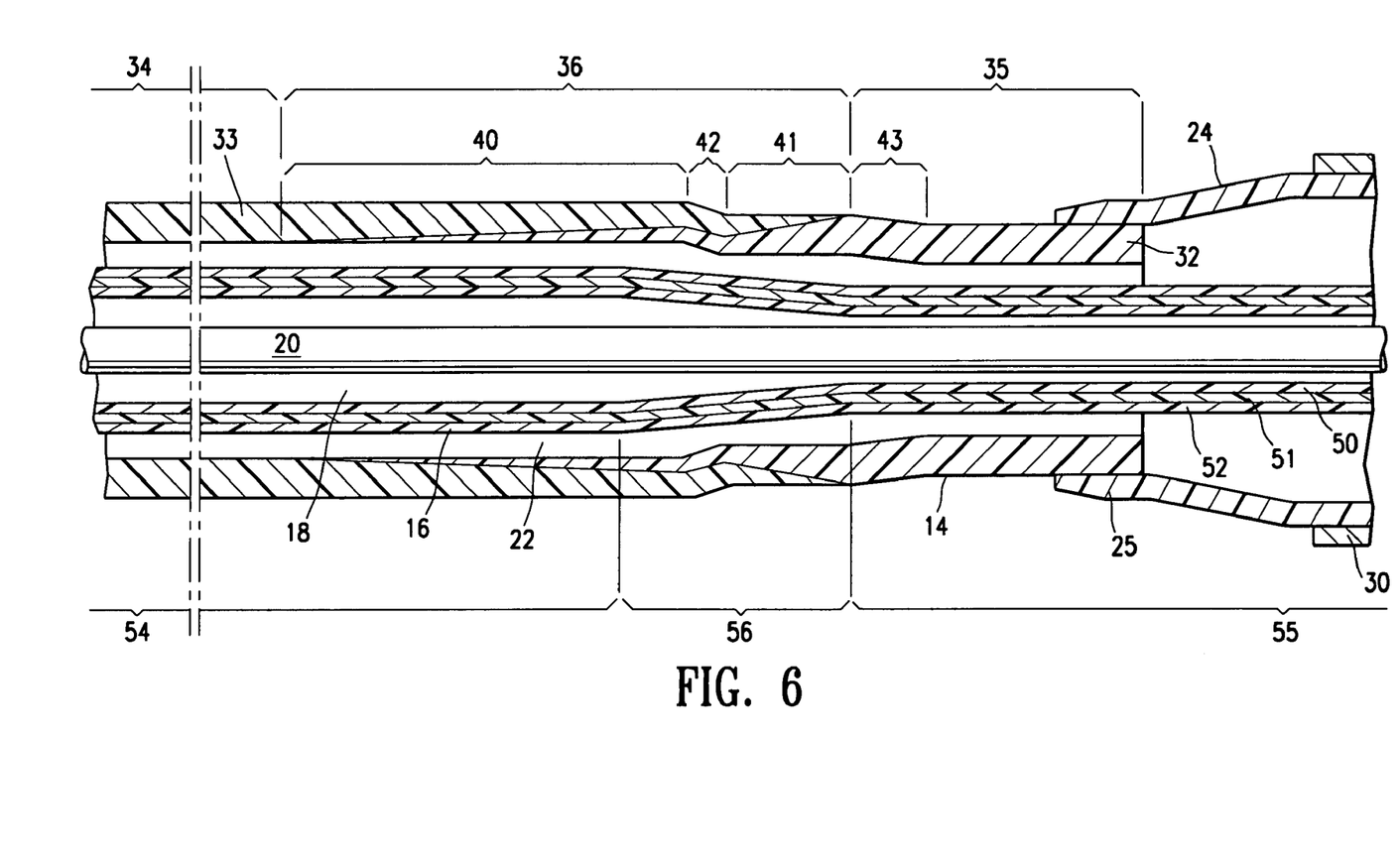
FIG. 6 an enlarged, longitudinal cross sectional partial view of an alternative embodiment of a balloon catheter embodying features of the invention, having the first and second layers of the outer tubular member extending less than the entire length of the outer tubular member

In the embodiment of FIG. 2, the inner and outer layers 32, 33 extend the entire length of the outer tubular member 14. In alternative embodiments, one or both of the layers 32, 33 are shorter than the length of the outer tubular member 14. For example, FIG. 6 illustrates an enlarged, longitudinal cross sectional partial view of an alternative embodiment of a balloon catheter embodying features of the invention, having first and second layers 32, 33 of the outer tubular member 14 extending less than the entire length of the outer tubular member 14. Specifically, the first (e.g., inner) layer 32 extends only along the distal section 34 and the transition section 36, whereas the second (e.g., outer) layer 33 extends only along the proximal section 35 and the transition section 36. Thus, the relative proportion of the first and second layers 32, 33 along the proximal section 35 is 0:100, and the relative proportion of the first and second layers 32, 33 along the distal section is 100:0. The layers 32, 33 inversely cotaper along the transition section 36, with the first layer 32 proximal end located at the proximal end of the transition section 36, and with the second layer 33 distal end located at the distal end of the transition section 36. In alternative embodiments, one of the layers 32, 33 extends beyond the transition section 36, as for example in an embodiment (not shown) similar to the embodiment of FIG. 6 but having the second layer 33 extending together with the first layer 32 along all or part of the distal section 35 (beyond the distal end of the transition section 36), in the second relative proportion as discussed above in relation to the embodiment of FIG. 2.

The first layer 32 is formed of a first polymer having a lower Shore durometer hardness than the second layer 33. In embodiment illustrated in FIG. 6, the first layer 32 is an inner layer relative to the second layer 33 along the transition section 36, although in alternative embodiments (not shown) it is an outer layer relative to the second layer 33. Similar to the embodiment of FIG. 2, the inner and outer diameter of the outer tubular member 14 decrease distally at tapered portion 42 of transition section 36, and at tapered portion 43 of distal section 35. Although both the inner and outer diameter of the outer tubular member 14 decrease along tapered portions 42, 43 in the embodiments of FIGS. 2 and 6, in an alternative embodiment (not shown), only the outer diameter decreases.

The dimensions of catheter 10 are determined largely by the size of the balloon and guidewire to be employed, the catheter type, and the size of the artery or other body lumen through which the catheter must pass or the size of the stent being delivered. The outer tubular member 14 generally has an outer diameter of about 0.025 to about 0.042 inch (0.064 to 0.11 cm), and a wall thickness of about 0.002 to about 0.008 inch (0.0051 to 0.02 cm), more specifically about 0.005 to 0.007 inch (0.013 to 0.018 cm). The inner tubular member 16 generally has an outer diameter of about 0.02 to about 0.03 inch (0.05 to 0.076 cm), and a wall thickness of about 0.004 to about 0.008 inch (0.01 to 0.02 cm). The overall length of the catheter 10 may range from about 100 to about 150 cm, and is typically about 143 cm. Balloon 24 typically has a length about 0.8 cm to about 6 cm, and an inflated working diameter of about 1.5 to about 10 mm.

Although the illustrated embodiment is an over-the-wire stent delivery catheter, the catheter of the invention may comprise other types of intravascular catheters, such as angioplasty catheters and rapid exchange balloon catheters. Rapid exchange catheters generally comprise a distal guidewire port in a distal end of the catheter, a proximal guidewire port in a distal shaft section and typically spaced a substantial distance from the proximal end of the catheter, and a short guidewire lumen extending between the proximal and distal guidewire ports in the distal section of the catheter. Thus, unlike the embodiment of FIG. 1, the inner tubular member 14 of a rapid exchange catheter embodiment (not shown) would extend from the distal guidewire port 21 to a proximal guidewire port spaced a substantial distance from the proximal end of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft comprising,
      i) a multilayered outer tubular member defining an inflation lumen, and having at least a first layer and a second layer, and the outer tubular member further having
         a relatively stiff proximal section with the first and second layers extending in a first relative proportion which is substantially constant;
         a relatively flexible distal section with the first and second layers extending in a second relative proportion which is substantially constant and which is different from the first relative proportion, the distal section having a tapered portion along which the outer diameter of the distal section decreases distally; and
         a transition section extending between and connecting a distal end of the proximal section and a proximal end of the distal section, along which the relative proportion of the first and second layers inversely cotapers to transition from the first to the second relative proportion, the transition section having a proximal portion, a distal portion, and a tapered portion along which the outer diameter of the transition section decreases distally; and
      ii) a multilayered inner tubular member extending at least in part in at least a distal section of the inflation lumen, and defining a guidewire lumen, and having a proximal section, a distal section, and a tapered section extending between and connecting a distal end of the proximal section and a proximal end of the distal section and along which the outer diameter of the inner tubular member decreases distally, and wherein a proximal end of the inner tubular member tapered section is radially aligned with a location on the outer tubular member located in the proximal portion of the transition section of the outer tubular member; and
   b) a balloon secured to the catheter shaft, having an interior in fluid communication with the inflation lumen.

2. The balloon catheter of claim 1 wherein a distal end of the tapered section of the inner tubular member is radially aligned with a location on the outer tubular member located at a proximal end of the tapered portion of the distal section of the outer tubular member.

3. The balloon catheter of claim 1 wherein the entire length of the inner tubular member tapered section is radially aligned with a location on the outer tubular member located in the transition section of the outer tubular member.

4. The balloon catheter of claim 1 wherein the outer tubular member first layer is an inner layer and the outer tubular member second layer is an outer layer, and the outer layer has a higher Shore durometer hardness than the inner layer.

5. The balloon catheter of claim 4 wherein the first relative proportion of the inner and outer layers of the outer tubular member is about 5:95 to about 40:60.

6. The balloon catheter of claim 4 wherein the first relative proportion of the inner and outer layers of the outer tubular member is about 20:80 to about 30:70.

7. The balloon catheter of claim 5 wherein the second relative proportion of the inner and outer layers of the outer tubular member is about 40:60 to about 95:5.

8. The balloon catheter of claim 5 wherein the second relative proportion of the inner and outer layers of the outer tubular member is about 45:55 to about 55:45.

9. The balloon catheter of claim 1 wherein the inner tubular member has three layers of different polymeric materials extending from a proximal end to a distal end of the inner tubular member in a constant relative proportion.

10. The balloon catheter of claim 1 wherein the entire length of the outer tubular member transition section is less than the entire length of the outer tubular member proximal section and greater than the entire length of the outer tubular member distal section.

11. The balloon catheter of claim 1 wherein the entire length of the tapered portion of the outer tubular member transition section is about 5% to about 10% of the entire length of the transition section of the outer tubular member.

12. The balloon catheter of claim 1 wherein the entire length of the tapered portion of the outer tubular member distal section is about 15% to about 50% of the entire length of the distal section of the outer tubular member.

13. The balloon catheter of claim 1 wherein the entire length of the tapered section of the inner tubular member is about 10% to about 25% of the entire length of the inner tubular member.

14. The balloon catheter of claim 1 wherein the inner diameter of the transition section decreases distally along the tapered portion thereof.

15. The balloon catheter of claim 1 wherein the inner diameter of the distal section decreases distally along the tapered portion thereof.

16. A balloon catheter, comprising:
a) an elongated shaft comprising,
  i) a multilayered outer tubular member defining an inflation lumen, having an outer layer formed of a first polymeric material, and an inner layer formed of a second polymeric material having a lower Shore durometer hardness than the first polymeric material, and the outer tubular member further having
    a relatively stiff proximal section with the inner and outer layers extending in a substantially constant first relative proportion of about 25:75;
    a relatively flexible distal section with the inner and outer layers extending in a substantially constant second relative proportion of about 50:50, the distal section having a tapered portion along which the inner diameter and outer diameter of the distal section decrease distally; and
    a transition section extending between and connecting a distal end of the proximal section and a proximal end of the distal section, along which the relative proportion of the inner and outer layers inversely cotapers to transition from the first to the second relative proportion, the transition section having a proximal portion, a distal portion, and a tapered portion along which the inner diameter and outer diameter of the transition section decrease distally; and
  ii) a multilayered inner tubular member extending at least in part in the inflation lumen, and defining a guidewire lumen, and having a proximal section, a distal section, and a tapered section extending between and connecting a distal end of the proximal section and a proximal end of the distal section and along which the inner and outer diameter of the inner tubular member decrease distally, wherein the entire length of the tapered section of the inner tubular member is radially aligned with a location on the outer tubular member located in the transition section of the outer tubular member, and a distal end of the tapered section of the inner tubular member is radially aligned with a location on the outer tubular member located at a proximal end of the tapered portion of the distal section of the outer tubular member; and
b) a balloon secured to the catheter shaft, having an interior in fluid communication with the inflation lumen.

17. A balloon catheter, comprising:
a) an elongated shaft comprising,
  i) a multilayered outer tubular member defining an inflation lumen, and having at least a first layer formed of a first polymer, and a second layer formed of a second polymer having a lower Shore durometer hardness than the first polymer, and the outer tubular member further having
    a relatively stiff proximal section having the second layer extending therealong;
    a relatively flexible distal section having the first layer extending therealong, wherein the distal end of the second layer is in the transition section so that the second layer does not extend along the distal section of the outer tubular member, and the distal section has a tapered portion along which the outer diameter of the distal section decreases distally; and
    a transition section extending between and connecting a distal end of the proximal section and a proximal end of the distal section, along which the relative proportion of the first and second layers inversely cotapers, with the proximal end of the first layer being in the transition section, the transition section having a proximal portion, a distal portion, and a tapered portion along which the outer diameter of the transition section decreases distally; and
  ii) a multilayered inner tubular member extending at least in part in the inflation lumen, and defining a guidewire lumen, and having a proximal section, a distal section, and a tapered section extending between and connecting a distal end of the proximal section and a proximal end of the distal section and along which the inner diameter and outer diameter of the inner tubular member decrease distally; and b) a balloon secured to the catheter shaft, having an interior in fluid communication with the inflation lumen.

18. A balloon catheter, comprising:

a) an elongated shaft comprising, i) a multilayered outer tubular member defining an inflation lumen, and having at least a first layer formed of a first polymer, and a second layer formed of a second polymer having a lower Shore durometer hardness than the first polymer, and the outer tubular member further having       a relatively stiff proximal section having the second layer extending therealong;

a relatively flexible distal section having the first and the second layers extending along at least part of the distal section in a substantially constant relative proportion, wherein the distal end of the second layer is in the distal section, and the distal section has a tapered portion along which the outer diameter of the distal section decreases distally; and       a transition section extending between and connecting a distal end of the proximal section and a proximal end of the distal section, along which the relative proportion of the first and second layers inversely cotapers, with the proximal end of the first layer being in the transition section, the transition section having a proximal portion, a distal portion, and a tapered portion along which the outer diameter of the transition section decreases distally; and    ii) a multilayered inner tubular member extending at least in part in the inflation lumen, and defining a guidewire lumen, and having a proximal section, a distal section, and a tapered section extending between and connecting a distal end of the proximal section and a proximal end of the distal section and along which the inner diameter and outer diameter of the inner tubular member decrease distally; and b) a balloon secured to the catheter shaft, having an interior in fluid communication with the inflation lumen.

* * * * *